United States Patent [19]

Chiusole et al.

[11] Patent Number: 4,576,704

[45] Date of Patent: Mar. 18, 1986

[54] APPARATUS FOR THE ELECTROCHEMICAL DETECTION OF THE OXYGEN CONTENT OF LIQUIDS

[75] Inventors: Erwin Chiusole, Bregenz, Austria; Hans Züllig, Rheineck, Switzerland

[73] Assignee: Züllig AG Rheineck, Rheineck, Switzerland

[21] Appl. No.: 703,229

[22] PCT Filed: Dec. 12, 1983

[86] PCT No.: PCT/CH83/00139

§ 371 Date: Jan. 29, 1985

§ 102(e) Date: Jan. 29, 1985

[87] PCT Pub. No.: WO84/04814

PCT Pub. Date: Dec. 6, 1984

[30] Foreign Application Priority Data

Jun. 2, 1983 [CH] Switzerland .............. 3015/83

[51] Int. Cl.⁴ .............................. G01N 27/38
[52] U.S. Cl. .................................. 204/402
[58] Field of Search ..................... 204/402, 422

[56] References Cited

U.S. PATENT DOCUMENTS

| | | | |
|---|---|---|---|
| 1,668,434 | 5/1928 | Todd | 204/402 X |
| 3,155,603 | 11/1964 | Hart | 204/402 |
| 3,496,084 | 2/1970 | Stack, Jr. | 204/402 |
| 3,574,079 | 4/1971 | Kalman | 204/405 |
| 3,875,036 | 4/1975 | Morris et al. | 204/402 |
| 4,285,792 | 8/1981 | McGandy | 204/402 |

FOREIGN PATENT DOCUMENTS

| | | | |
|---|---|---|---|
| 2328921 | 1/1974 | Fed. Rep. of Germany | 204/402 |
| 469981 | 4/1969 | Switzerland | 204/402 |
| 2092306 | 8/1982 | United Kingdom | 204/402 |

Primary Examiner—John F. Niebling
Assistant Examiner—Nam X. Nguyen
Attorney, Agent, or Firm—Watson, Cole, Grindle & Watson

[57] ABSTRACT

In an apparatus for determining the oxygen content of a liquid by measuring the electric current between two electrodes (20, 21) of different materials which are immersed into the liquid, each electrode (20, 21) is embedded in its own body (18, 19) of insulating material in such a manner that only one end surface (20a, 21a) of each electrode is free and may be electrochemically active. The respective structural units (13, 14) consisting of an electrode and insulating body are pressed via associated springs (30, 31) at a common grinding device (28) displaceable by a driving apparatus, which grinding device serves for cleaning the free electrode end surfaces (20, 21a). The spring force by means of which the pressing to the grinding device (28) occurs is individually adjustable for each of the structural units (13, 14) by adjustment of a support ring (32, 35) for the relevant spring (30, 31) to match the hardness, abrasion-resistance and corrosion properties of the material of the revelant electrode.

7 Claims, 2 Drawing Figures

APPARATUS FOR THE ELECTROCHEMICAL DETECTION OF THE OXYGEN CONTENT OF LIQUIDS

BACKGROUND OF THE INVENTION

The present invention concerns apparatus for the electrochemical detection of the oxygen content of liquids by measurement of an electric current between two electrodes made from different materials immersed in the liquid, which electrodes are, with the exception of their effective free end surfaces, fully embedded in insulating material, wherein for cleaning the free electrode end surfaces a grinding device is pressed by means of at least one spring both to the free electrode end surfaces and to the adjacent surface area portions of the insulating material and the electrodes are so shaped and arranged that in the course of continued grinding of the electrodes and the insulating material, the shape, size and mutual spacing of the effective end surfaces remain unchanged.

An apparatus of the above type is disclosed in Swiss Pat. No. 469,981. According to this patent the two electrodes are formed by coaxially arranged pipe sections which are radially spaced apart, the pipe sections being fully embedded in an electrically insulating synthetic material body with the exception of one of their end surfaces lying on the same axial slide. To clean the effective, free electrode end surfaces a grinding organ is provided which is rotatable by a driving device around the axis of the tube sections, the grinding body having a grinding surface bearing against the free end surfaces of the pipe sections and the surface portions of the synthetic resin body adjacent to these end surfaces, and is pressed against the noted surfaces under the bias of a spring. Although this known apparatus has proved itself well in practice, it has a disadvantage which in certain circumstances is troublesome, i.e. because of the different hardness, abrasion-resistance and corrosion properties of the two electrodes consisting of different materials, a fully uniform wear or abrasion by means of the common grinding body is not always assured and various deposits of grinding particles may adhere to the free ends of the electrode end surfaces. This may result in variations in the electrochemical properties of the free electrode end surfaces, whereby the accuracy of the oxygen measurements is impaired or a frequent recalibration of the measurement apparatus becomes necessary.

SUMMARY OF THE INVENTION

Accordingly, the object of the present invention is to provide an apparatus of the above-described type which avoids the above-described disadvantage and provides an increased uniformity of the grinding-off and cleaning of the two free electrode end surfaces is assured by the common grinding device.

In the apparatus according to the invention each electrode is embedded in its own insulating body and forms with it a single structural unit which is pressed against the grinding device by means of at least one associated spring independently of the other structural unit, the designer has it under his control to bring about an optimal grinding and cleaning effect by the individual sizing or rating of the spring forces for each electrode and to do this despite the different hardness, abrasion resistance and corrosion properties of the two electrodes.

Further details and advantages of the invention will be clear from the following description of preferred embodiments as well as the associated drawing in which the invention is illustrated purely by way of example.

DESCRIPTION OF THE INVENTION

DETAILED DESCRIPTION OF THE PREFERRED EMBODIMENT

Figure 1:
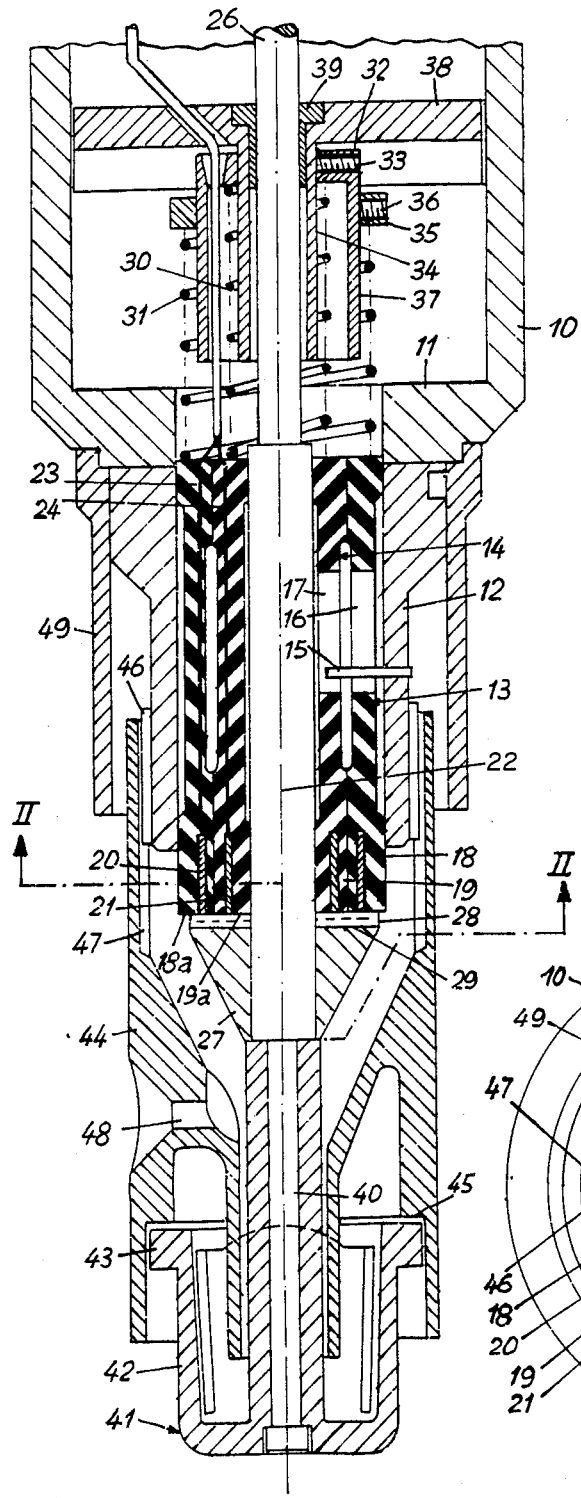
FIG. 1 shows an axial longitudinal section through the essential parts of apparatus formed according to the invention for the electrochemical measurement of the oxygen content in liquids.
Figure 2:
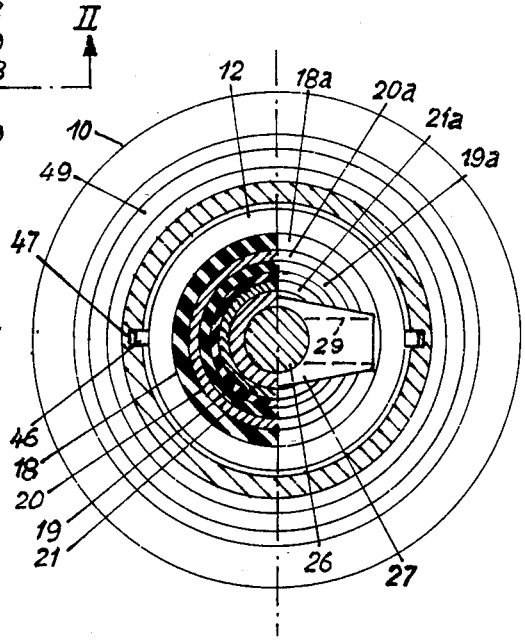
FIG. 2 represents a cross-section along the line II—II in FIG. 1.

The apparatus illustrated in the drawing has a vertically extending carrier pipe 10 which is provided at its lower end with an inwardly projecting flange 11. A sleeve-shaped guide housing 12 is secured at the flange 11 and in it are disposed two sleeve rings 13 and 14 of which one is coaxially disposed in the other. The outer sleeve ring 13 is axially displaceably guided in the guide housing 12 and the inner sleeve ring 14 is also axially displaceable relative to the outer sleeve ring 13. Both the sleeve rings 13 and 14 are secured against rotation, e.g., by virtue of the fact that a pin 15 inserted radially in the guide housing 12 engages in longitudinal slits 16, 17 of the sleeve rings 13 and 14 respectively. Self-evidently, other known measures for securing the sleeve rings 13 and 14 against rotation may also be suitable.

Each of the sleeve rings 13 and 14 constitutes a structural unit formed from a body 18, 19 of insulating material and an electrode 20, 21 embedded therein, respectively. The electrodes 20 and 21 consisting of different materials have the form of coaxially arranged pipe pieces. It may be seen from FIG. 1 that with the exception of the lower axial end surfaces 20a and 21a, all the surface portions of the electrodes 20 and 21 lie within the insulating body 18, 19, respectively, and the free electrode end surfaces 20a and 20a together with the adjacent lower end surfaces 18a and 19a of the insulating bodies 18 and 19 lie in the same plane, this plane being perpendicular to the common geometrical longitudinal axis 22 of the guide casing 12, the sleeve rings 13 and 14 and the electrodes 20 and 21. Each insulating body 18, 19 contains a respective electrical conductor 23, 24 which is connected on the one hand to the relevant electrode 20, 21 and on the other hand leads to an indicating and/or recording instrument not shown in the drawing. Preferably, the inner electrode 21 consists of a silver-mercury alloy while the other electrode 20 may consist of iron, zinc or gold.

A rotatable shaft 26 carrying a holder 27 for a grinding device 28 projects through the inner sleeve ring 14. A holder 27 is connected fast in rotation with the shaft 26 and at its side which is shown at the top in FIG. 1 has a groove 29 extending radially with respect to the shaft 26, the (two part) grinding device 28 being inserted into this groove. The grinding device bears against the lower end surfaces 18, 20a and 19a, 21a of the sleeve rings 13 and 14, respectively. The upper end of the shaft 26 is connected with a non-illustrated driving unit by means of which the shaft 26 and the grinding device 28 may be set into rotation. In order to produce the necessary pressure force between the grinding device 28 and the sleeve rings 13 and 14, two coil compression springs of different diameter are provided, the springs being arranged coaxially with the shaft 27 above the sleeve rings 13 and 14. The inner coil spring 30 bears with its lower end against the upper end of the inner sleeve ring 14 and with its upper end against a support ring 32 which sits on a sleeve 34 surrounding the shaft 26, the ring being displaceable in an axial direction and being securable by means of a grub screw 33. The sleeve 34 forms a radial guide for a few turns of the coil spring 30. Analogously, the lower end of the outer coil spring 31 bears against the upper end of the outer sleeve ring 13 while its upper end bears against a second supporting ring 35 disposed on a sleeve 37, the supporting ring being axially adjustable and securable by means of a grub screw 36. The sleeve 37 is connected with the first-mentioned supporting ring 32 and forms a radial guide for a few turns of the outer coil spring 31. The above mentioned sleeve 34 is connected with an annular disc 38 secured in the carrier pipe 10 axially and radially to support a collar 39 fast with the shaft 26 so that the collar 39 is rotatable relative to the annular disc 38.

A cup-like end part 41 provided with an upwardly projecting peripheral wall 42 with a flange 43 is secured by means of a bolt 40 to the lower end of the shaft 26. A jacket 44 surrounding the guide housing 12 with some radial play is supported via a shoulder 45 on the flange 43 of the end part 41. The jacket 44 is displaceable in an axial direction but is secured against rotation by virtue of the fact that outwardly projecting longitudinal ribs 46 of the guide housing 12 engage in corresponding longitudinal grooves 47 on the inside of the jacket 44. The shoulder 45 of the jacket 44 and the surfaces of the flange 43 of the end part 41 which support the shoulder 45 do not extend in a plane which is perpendicular to the geometrical axis 22 of the shaft 26, but rather have a construction such that on rotation of the end part 41, automatic axial reciprocating movement, that is up and down movement, of the jacket 44 is generated. The interior of the jacket 44 is shaped as a funnel and has at least one radial throughflow opening 48 through which a liquid, the oxygen content of which is to be determined, may enter into the interior of the jacket and may arrive to the free end surfaces 20a and 21a of the electrodes 20 and 21, respectively. The upper end portion of the jacket 44 is surrounded by an apron with a radial gap therebetween, the apron being connected with the upper end part of the guide housing 12 and joins to the carrier pipe 10.

The manner of use and operation of the above-described apparatus is in brief as follows:

The apparatus is immersed into the liquid to be investigated at least so deeply that the jacket 44 is fully surrounded by the liquid. The electrical conductors 23 and 24 are connected with a suitable current indicating and/or recording instrument and the shaft 26 is set by means of the non-illustrated driving device into constant rotation of, e.g., about 10 revolutions per minute.

The rotation of the shaft 26 imparts periodic lifting and lowering movements to the jacket 44 whereby the free space between the jacket and the parts of the apparatus surrounded thereby is periodically reduced and enlarged in size. From this, a pumping effect results which has the consequence of periodic sucking-in and expulsion of the liquid through the opening 48 whereby the liquid standing in contact with the free end surfaces 20a and 21a of the electrodes 20 and 21 is continually renewed. At the same time, rotation of the shaft 26 rotates the grinding device 28 which continually spreads over the free end surfaces 20a and 21a of the electrodes 20 and 21 as well as the adjacent surfaces 18a and 19a of the insulating bodies 18 and 19 and gradually grinds them whereby the free electrode end surfaces 20a and 21a active in the electrochemical oxygen measurement are continually cleaned. In this way, a progressive wear of the electrodes 20 and 21 as well as the insulating bodies 18 and 19 takes place but the shape, dimensions and mutual spacing of the free electrode end surfaces 20a and 21a remain nevertheless unchanged and consequently, through the grinding no harmful influence on the oxygen measurement results.

By an axial adjustment of the support rings 32 and 35, the tension of the coil springs 30 and 31, and thus the pressing force with which the sleeve rings 13 and 14 are pressed against the grinding device 28, may be individually adjusted. In this way it is possible to match the pressing force to the mechanical properties of two different electrodes 20 and 21 in such a way that an optimal grinding and cleaning effect is achieved for both electrodes, whereby an improvement in the long-term stability of the measuring apparatus is obtained and the periods between the required recalibrations are extended.

In a non-illustrated constructional variant of the described apparatus the support rings 32 and 35 provided with adjusting screws 33 and 36 may be replaced by lock-nuts, each of which is disposed on an outer threading of the relevant sleeve 34, 37, respectively, and which are axially adjustable by rotation. Numerous other constructional solutions are also possible for the individual adjustment of the spring forces with which the sleeve rings 13 and 14 are pressed against the common grinding device 28. In given cases, it is sufficient to make the tension of only one of the springs adjustable. It is also possible to provide two or more springs for each of the sleeve rings 13 and 14, of which not all need to be adjustable. Finally, an embodiment may also be mentioned wherein one of the sleeve rings 13 and 14 is axially fixedly arranged while the grinding device 28 or its carrier 27 or the shaft 26 are axially displaceable and forced under the bias of a spring against the stationary sleeve ring, while the other sleeve ring is pressed by way of at least one associated other spring to the grinding device.

We claim:

1. In an apparatus for the electrochemical measurement of the oxygen content of liquids, said apparatus including first and second electrodes whose free ends can be immersed in the liquid whose oxygen content is to be measured, the oxygen content of the liquid being measured by an electric current occurring between the two electrodes, the apparatus also including a rotatable grinding device which can contact the free ends of said electrodes to clean them while the shape, size and mutual spacing of the free ends of said electrodes remain unchanged, the improvement wherein said first and second electrodes are embedded in respective first and second annular bodies of insulating material, each of said first and second annular bodies having an axial end surface which faces the liquid whose oxygen content is to be measured, the free ends of said first and second electrodes being exposed at the axial end surface of the respective annular body in which it is embedded, said first and second annular bodies being axially movable relative to one another, said apparatus includes first and second spring means which respectively cooperate with said first and second annular bodies to individually bias their said axial end surfaces toward said rotatable grinding device, and said apparatus includes at least one adjusting means for determining the biasing force of one of said first and second spring means exerted on its associated annular body, adjustment of said adjusting means enabling a uniform cleaning of the free ends of said two electrodes by said grinding device.

2. The apparatus as defined in claim 1, including a housing in which said first and second annular bodies are located, said housing including an opening therein; wherein each of said first and second annular bodies includes an axial slot therein; and including a pin means which is extendable through said opening in said housing to engage in the axial slot in each of said first and second annular bodies to prevent them from rotating while allowing axial displacement thereof.

3. The apparatus as defined in claim 2, including a rotatable shaft connected to said rotatable grinding device, said rotatable shaft coaxially extending through said first and second annular bodies.

4. The apparatus as defined in claim 3, wherein said first and second spring means comprise respective first and second helical compression springs which coaxially surround said rotatable shaft, each helical compression spring having a first end which contacts its associated annular body and an opposite second end.

5. The apparatus as defined in claim 4, including two adjusting means, a first adjusting means for said first helical compression spring means and a second adjusting means for said second helical compression spring.

6. The apparatus as defined in claim 5, wherein each of said two adjusting means comprises a support ring which is axially adjustably positionable with respect to said housing, each support ring contacting the second end of an associated helical compression spring.

7. The apparatus as defined in claim 6 wherein said first and second annular bodies comprise substantially cylindrical outer and inner sleeves.

* * * * *